United States Patent [19]
Buck et al.

[11] Patent Number: 5,055,560
[45] Date of Patent: * Oct. 8, 1991

[54] L60: A NOVEL MONOCLONAL ANTIBODY

[75] Inventors: David W. Buck, El Granada; Jane M. Bindl, Los Altos, both of Calif.

[73] Assignee: Becton Dickinson and Company, Franklin Lakes, N.J.

[*] Notice: The portion of the term of this patent subsequent to Jul. 31, 2007 has been disclaimed.

[21] Appl. No.: 481,030

[22] Filed: Feb. 16, 1990

Related U.S. Application Data

[63] Continuation of Ser. No. 139,491, Dec. 30, 1987, Pat. No. 4,945,056.

[51] Int. Cl.$^5$ .................. C12P 21/08; G01N 33/53; G01N 33/577
[52] U.S. Cl. .................. 530/387; 435/70.21; 435/172.2; 435/240.27; 435/942; 435/7.24; 935/102
[58] Field of Search .................. 435/240.27; 530/387; 935/103

Primary Examiner—Robert A. Wax
Assistant Examiner—M. P. Woodward
Attorney, Agent, or Firm—Robert M. Hallenbeck

[57] ABSTRACT

L60 is a novel monoclonal antibody that will react with Leu 22. It is equally reactive in formalin, ZnSO$_4$ or Bouin's fixed, paraffin-embedded tissues as well as in frozen tissues.

1 Claim, 1 Drawing Sheet

L60: A NOVEL MONOCLONAL ANTIBODY

This is a continuation of application Ser. No. 139,491, filed Dec. 30, 1987, which issued as U.S. Pat. No. 4,945,056 on July 31, 1990.

FIELD OF THE INVENTION

The present invention relates to the detection of the Leu 22 antigen, and more particularly, relates to the use of a novel monoclonal antibody (L60) which will bind to the Leu 22 antigen in frozen and in formalin, $ZnSO_4$ and Bouin's fixed, paraffin-embedded tissues.

BACKGROUND OF THE INVENTION

The vast majority of leukocyte antigens are destroyed by routine processing to paraffin blocks. As a result, the use of monoclonal antibodies (MAbs) to identify cell lineage, cell differentiation and cell subset populations have been restricted to fresh frozen tissue sections. In many instances, however, fresh frozen tissue sections may not be available for analysis. It is desirable, therefore, to find and identify MAbs that will react with leukocyte antigens in routinely processed, paraffin-embedded tissues.

Currently on the market are several monoclonal antibodies purportedly constructed to satisfy this desire. Among these antibodies are: Clonab MT1, MT2, MB1 and MB2 (available from BioTest, Inc.); LN1, LN2 and LN3 (available from Techniclone International); and Dako LC and UCHL-1 (available from Dako Corp.). Descriptions of each group of monoclonal antibodies have been reported in: Poppema et al., Monoclonal Antibodies (MT1, MT2, MB1, MB2,) Reactive with Leukocyte Subsets in Paraffin-Embedded Tissue Sections, Am. J. Pathol., 127:418–429 (1987); Epstein et al., Two New Monoclonal Antibodies (LN-1, LN-2) Reactive in B5 Formalin-Fixed, Paraffin-Embedded Tissues with Follicular Center and Mantle Zone Human B Lymphocytes and Derived Tumors, J. Immunol., 133:1028–1036 (1984); and Norton et al., Momoclonal Antibody (UCHL1) that Recognizes Normal and Neoplastic T Cells in Routinely Fixed Tissues, J. Clin. Pathol., 39:399–405 (1986).

Although these MAbs function in other than frozen tissue sections, the antigens they react with are of limited use both in terms of their distribution and specificity. A number of these MAbs will cross-react between T and B cell lines, for example. Thus, the usefulness of these MAbs is somewhat limited.

It would be desirable, therefore, to find an antigen that is distributed on T cell malignancies but not on B cell malignancies. This is of clinical importance because T cell malignancies behave more aggressively than B cell malignancies, and thus, require more aggressive treatment.

Similarly, the diagnosis of Hodgkin's from non-Hodgkin's lymphomas is important because of the vast prognostic and therapeutic differences between the diagnostic alternatives. For determination of Hodgkin's versus non-Hodgkin's lymphomas, therefore, it would be useful to have a monoclonal antibody that would identify an antigen that discriminates between Hodgkin's and non-Hodgkin's lymphomas.

Leu 22 is antigen of approximately 100 kD that is found on normal and malignant T cells, peripheral blood monocytes and a subpopulation of normal B cells and tissue macrophages. It is conserved on non-Hodgkin's lymphomas of T cell origin but is not found on Reed-Sternberg cells in Hodgkin's disease. Thus, the Leu 22 antigen has many of the characteristics desired.

BRIEF DESCRIPTION OF THE INVENTION

L60 is monoclonal antibody that recognizes the Leu 22 antigen on T cells, blood monocytes, tissue macrophages and on a subpopulation of B cells. It was derived from a mouse hybridoma clone DB38.3E3. The hybridoma was formed between spleen cells from Balb/c mice immunized with phytohemagglutinin(PHA) activated T cells and the murine plasmacytoma cell line SP2/0 AG 14. L60 is an $IgG_{1k}$ type monoclonal antibody. L60 reacts with T lymphomas fixed in either formalin, $ZnSO_4$ or Bouin's fixative. It is useful in distinguishing Hodgkin's from non-Hodgkin's lymphomas.

DETAILED DESCRIPTION OF THE INVENTION

Figure 1:
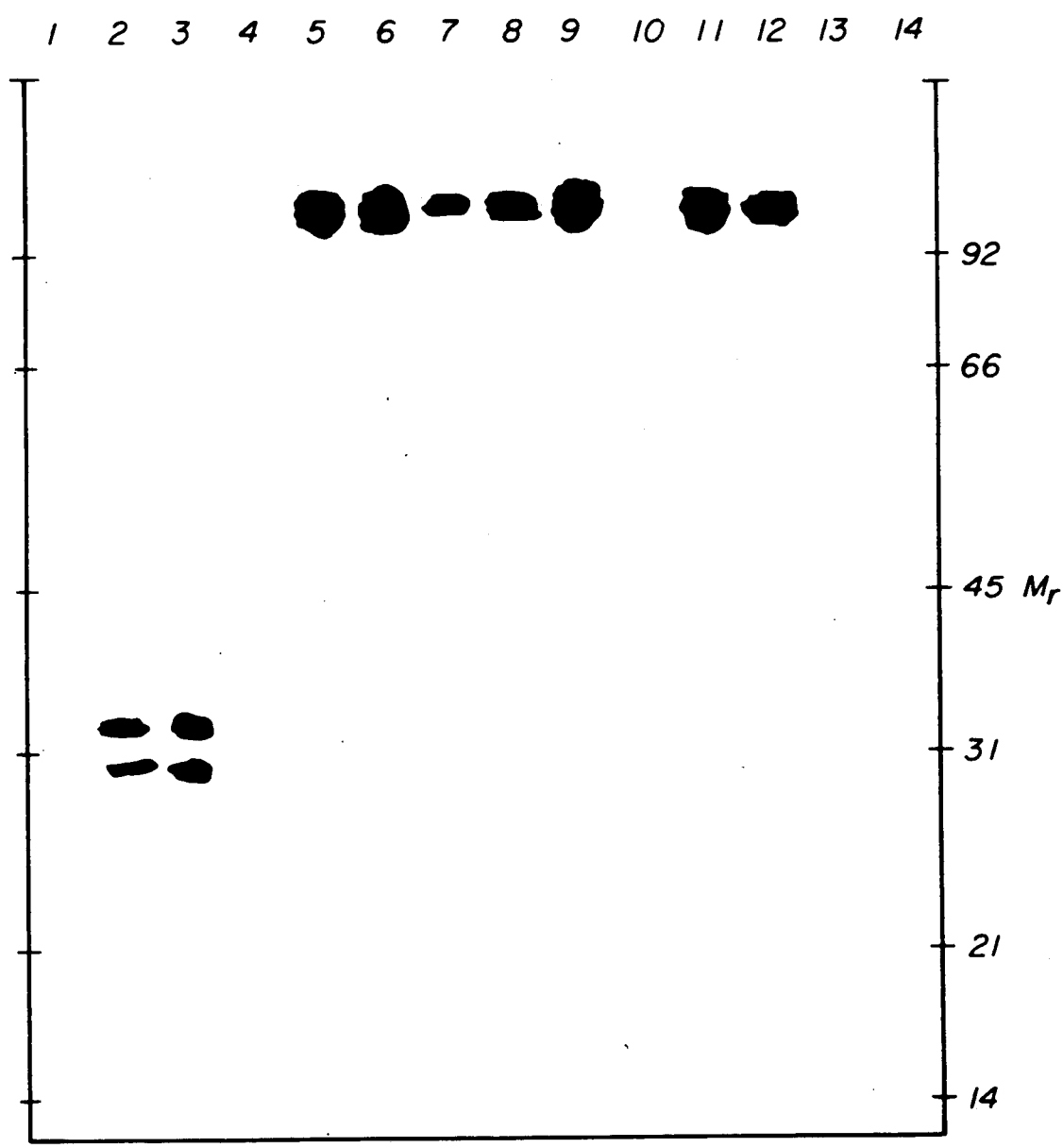
FIG. 1 is a rendering of an autoradiograph of a 10% SDS/PAGE gel wherein HPB-ALL cells were reacted with Anti-Leu 22 or with one of several controls or L60 like clones by the lactoperoxidase/glucose oxidase method and were labeled with $^{125}I$. Material then was applied to the gel and run as follows: Lane 1—gamma 1 control; Lane 2—Anti-Leu 2a; Lane 3—Anti-Leu 2; Lane 4—Anti-Leu 2c; Lane 5—Anti-Leu 22 (supernatant from mouse culture); Lanes 6–8 and 10–11—L60 like clones (L60.1, 7D12, 7D12.12, L50 and L51 respectively); Lane 9—1G10 (a gamma 2a, L60 like clone); and Lane 10—1G11. Lanes 13 and 14 were not used.

The L60 monoclonal antibody was prepared as follows. T lymphocytes were isolated from human peripheral blood by density dependent centrifugation on Ficoll-Hypaque (Litton Bionetics). T cells were cultured in RPMI 1640 (GIBCO) and 10% fetal calf serum (FCS) to which 1.0% PHA was added. After 72 hours, $1 \times 10^7$ PHA-activated T cells were injected intraperitoneal ("I/P") into a Balb/c mouse. On day 19, the mouse was boosted I/P with $1 \times 10^7$ PHA-activated T cells. On day 78, the mouse was boosted with $4 \times 10^6$ PHA-activated T cells intravenous ("I/V").

On day 81, the mouse was sacrificed and the spleen excised. Splenocytes then were fused with the continuous plasmacytoma fusion partner SP2/0 Ag 14, Shulman et al., Nature, 276:269 (1978), in 35% polyethylene glycol. Similar procedures for preparations of spleen cells and fusion have been previously described in U.S. Pat. Nos. 4,172,124 and 4,196,265 which are incorporated herein by reference.

Viable cells resulting from the fusion process were plated in 96 well microculture plates (B-D Falcon) in Dulbecco's Modified Eagle's Medium (GIBCO) containing 20% fetal calf serum ("FCS"). A solution of 15 mM HEPES (GIBCO) and azaserine-hypoxanthine (2 ug/ml and $10^{-4}M$ final concentration respectively) was added to each well as a selection media according to the procedures of Buck et al., Production of Human Monoclonal Antibodies, in Monoclonal Antibodies and Functional Cell Lines, Plenum Publishing Corp. (Kennett et al., eds) (1984). hybridomas grown in this medium may be separated from unfused myeloma cells and spleen cells which die shortly after fusion. Incubation continued for 7–10 days or until visible colonies appeared.

Hybridoma supernatants initially were characterized by binding to PHA-activated T cells and non-binding to the LB B cell line (a lymphoblastoid cell line) using a Pandex ™ screening device (Pandex Laboratories, Inc.). $1 \times 10^5$ PHA-activated T cells or LB B cells were added to each well of a 96 well Pandex ™ plate. To each well was added 30 ul of supernatant. After 30 minutes, the cells were washed in 0.15M phosphate buffered saline (PBS). Goat anti-mouse Ig antibody coupled to fluorescein isothiocyanate (GAMIg-FITC, Becton Dickinson Immunocytometry Systems) then was added to each well, incubated and the results were read on the Pandex screening device.

Cells from those wells whose supernatants tested positive were replated in 24 well microculture plates and grown in Dulbecco's Modified Eagle's Medium (M.A. Bioproducts) containing hypoxanthine and 20% FCS. Supernatants from each well were added to wells containing either PHA-activated T cells or LB B cells. GAMIg-FITC again was added. Stained cells from these wells were subjected to analyses by flow cytometry instrumentation (FACScan ™, Becton Dickinson Immunocytometry Systems). Cells were examined for forward and right angle light scatter and fluorescence. From the analyses, clone DB38.3E3 was selected. It has been deposited with American Type Culture Collection, Rockville, Md., under the terms of the Budapest Treaty on Oct. 20, 1987 as accession number HB-9575.

The monoclonal antibody produced by this clone has been designated L60. It also may be referred to as Anti-Leu 22. It has an isotype of $IgG_{1k}$. It will immunoprecipitate an antigen on mitogen activated or resting T cells of approximately 100 kD under reducing conditions. See FIG. 1. This antigen has been designated Leu 22. It is not, however, the T-200 antigen. Immunoperoxidase staining of normal tissue shows that L60 strongly reacts with T cells and macrophages in tonsil, cortical and medullary thymocytes in thymus, and T cells in spleen.

To demonstrate its ability to identify Leu 22 in fixed, paraffin-embedded tissues, L60 was reacted with a variety of tissue specimens and detected using a two-step indirect staining technique. Tissue sections were fixed in formalin, $ZnSO_4$ or Bouin's and embedded in paraffin in accordance with standard procedures. The tissues had been excised from patients with a variety of lymphomas.

5 um paraffin tissue sections were cut and floated on a water bath containing gelatin and chromium potassium sulfate. The sections then were applied to slides and dried. The sections then were deparaffinized by placing them in 4 changes of Histoclear ™ (National Diagnostics), followed by several changes in a graded ethanol series, distilled water and 0.1M phosphate buffered saline (PBS). Routinely, sections were next treated to block endogenous peroxidase by placing the section in 3% aqueous $H_2O_2$ for 5 minutes. Sections then were rinsed in 0.1M PBS. After rinsing, sections were incubated with the approriate monoclonal antibody in a humified chamber to avoid drying. After incubation, the sections were rinsed in PBS.

At this stage, it is important to add a blocking serum. A 1:10 dilution of normal goat serum was applied for 40 minutes. Excess serum was removed by wiping around the section only. Rinsing is to be avoided.

Once the excess serum is removed, horseradish peroxidase conjugated goat anti-mouse IgG (Vector) in PBS containing 0.1% thimerosal (Sigma), 0.2% gelatin and 5% normal human serum is applied for 40 minutes. The section again was rinsed in PBS as above.

Alternatively, biotin conjugated horse anti-mouse IgG followed by horseradish peroxidase conjugated avidin (Vector) may be used in a three step procedure in place of the two step secondary antibody enzyme combination.

Once the sections have been incubated with the horseradish perixidase conjugate, enough 3.3 Diaminobenzidine (DAB, Sigma) in 10 ul of 30% $H_2O_2$ and 1 ml of 0.1 PBS was added to cover the section for 5 minutes. The section then was rinsed in PBS as above.

Once rinsed, the section was treated with a 0.5% solution of $CuSO_4$ in 0.85% NaCl for 5 minutes. The section then was rinsed in distilled water. The section then was counterstained in Gill's Progressive Hematoxylin (4.0 gm hematoxylin [Sigma], 0.4 gm $NaIO_3$, 70.4 gm $Al_2(SO_4)_3 18H_2O$, 20 ml glacial acetic acid) for 30 seconds, and rinsed in tap water.

The section then was dipped in a saturated solution of aqueous lithium carbonate until blue. The section again was rinsed in tap water, and dehydrated in alcohol, Histoclear ™ and xylene and coverslipped in a resinous mounting media. The section then was ready for microscope examination.

If frozen sections were used, 4–5 um cryostat sections were air dried for 2 hours. The sections must be thoroughly dry. Dried sections were applied to slides pretreated with a chrom alum-gelatin solution, and were then fixed in reagent grade acetone at room temperature for 10 minutes then air dried. The sections then were stained immediately as above, with the exceptions that counterstaining should be done for 1 minute and dipping in lithium carbonate was omitted. If the sections were not used immediately, they were stored at $-70°$ C. with a desiccant. Stored sections should come to room temperature in the presence of a desiccant prior to staining.

Table 1 sets forth the lymphomas examined using the above procedures. The lymphoma type was determined in accordance with standard pathologic procedures. The number of lymphomas examined and reactive with L60 is given. "ND" indicates that the results were not determined. As evident from Table 1, L60 is reactive in several paraffin-embedded tissues from T cell but not B cell lymphomas.

TABLE 1

| | L60 Positive | |
| | Lymphoma Type | |
| Fixative | T Cell | B Cell |
| --- | --- | --- |
| Bouin's | 6/8 | ND |
| Formalin | 5/5 | 0/5 |
| $ZnSO_4$ | 5/11 | ND |

Variations and modifications of the above described invention may suggest themselves to those skilled in the art. Accordingly, the description should not be taken in any limiting sense.

What is claimed is:

1. A monoclonal antibody capable of reacting with the same antigen as that recognized by an antibody produced by the hybridoma deposited as ATCC HB-9575.

* * * * *